9/87 128/660 OR 4,671,293

United States Patent [19]

Shaulov

[11] Patent Number: 4,671,293

[45] Date of Patent: Jun. 9, 1987

[54] BIPLANE PHASED ARRAY FOR ULTRASONIC MEDICAL IMAGING

[75] Inventor: Avner A. Shaulov, Monsey, N.Y.

[73] Assignee: North American Philips Corporation, New York, N.Y.

[21] Appl. No.: 787,409

[22] Filed: Oct. 15, 1985

[51] Int. Cl.[4] .......... A61B 10/00

[52] U.S. Cl. .......... 128/660

[58] Field of Search .......... 128/660–661, 128/663; 310/334–336, 368; 73/625–626; 367/103, 105

[56] References Cited

U.S. PATENT DOCUMENTS

| | | | |
|---|---|---|---|
| 4,112,411 | 5/1978 | Alais et al. | 340/1 R |
| 4,156,158 | 5/1979 | Wilson et al. | 310/334 X |
| 4,211,948 | 7/1980 | Smith et al. | 310/334 X |
| 4,324,142 | 4/1982 | Auphan et al. | 73/626 |
| 4,344,159 | 8/1982 | Ballinger | 128/660 X |
| 4,455,503 | 6/1984 | Nakatani | 310/368 |
| 4,514,247 | 4/1985 | Zola | 156/250 |
| 4,518,889 | 5/1985 | 'T Hoen | 310/334 X |

OTHER PUBLICATIONS

"Properties of Composite Piezoelectric Materials for Ultrasonic Transducers' W. A. Smith et al., 1984 IEEE Ultrasonics Symposium, Dec. 1984.

"Performance of Ultrasonic Transducers Made from Composite Piezoelectric Materials", A. A. Shoulov et al., 1984 IEEE Ultrasonics Symposium, Dec. 1984.

*Primary Examiner*—Kyle L. Howell
*Assistant Examiner*—Francis J. Jaworski
*Attorney, Agent, or Firm*—Jack E. Haken; James J. Cannon, Jr.

[57] ABSTRACT

An improved biplane phased array transducer for real time medical imaging in at least two sector planes having a composite piezoelectric plate with an array of transducer elements disposed on each major surface of said plate, the array on one side being at an angle to the array on the other side, said transducer elements being defined by dicing each major surface of said composite plate through the conductive electrode surface and into a portion of the composite piezoelectric material, and electrical connections provided whereby each array may be grounded alternately so that real time sector imaging in two planes is obtained.

6 Claims, 7 Drawing Figures

FIG.1a
PRIOR ART
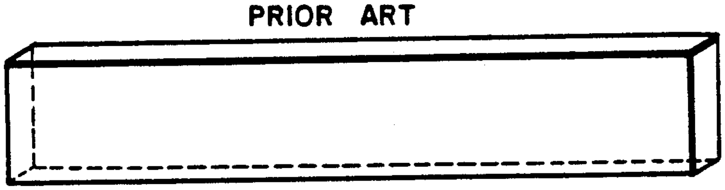
FIG.1b
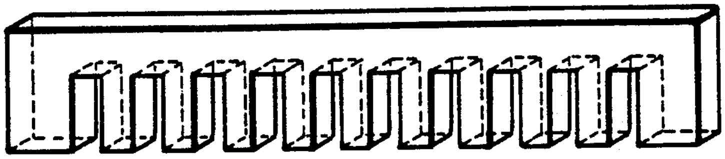
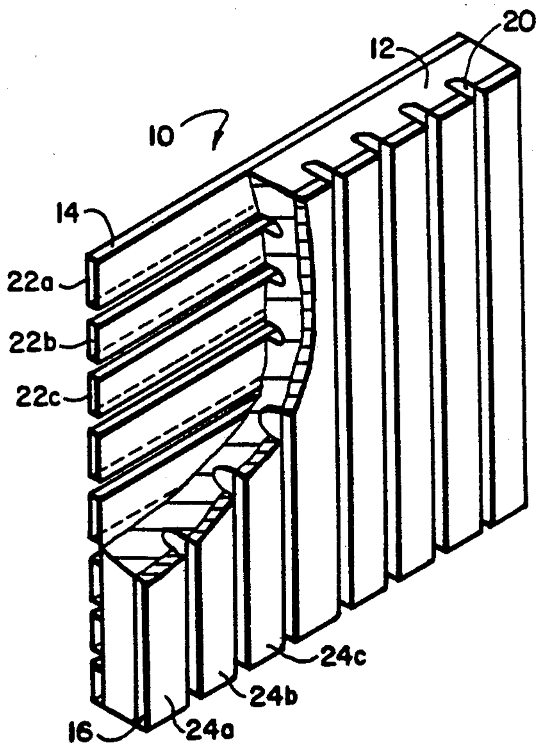
FIG.2

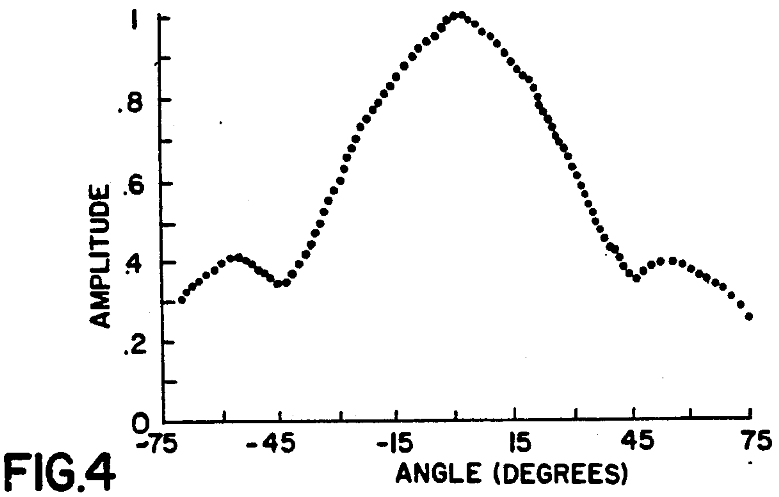
FIG.4
FIG.5
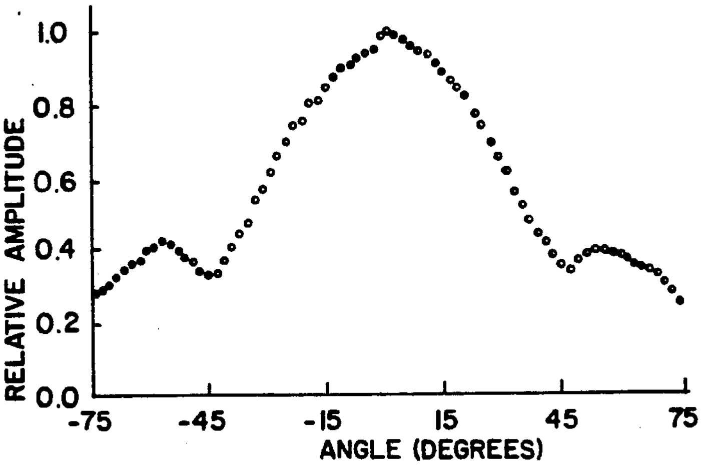
FIG.6
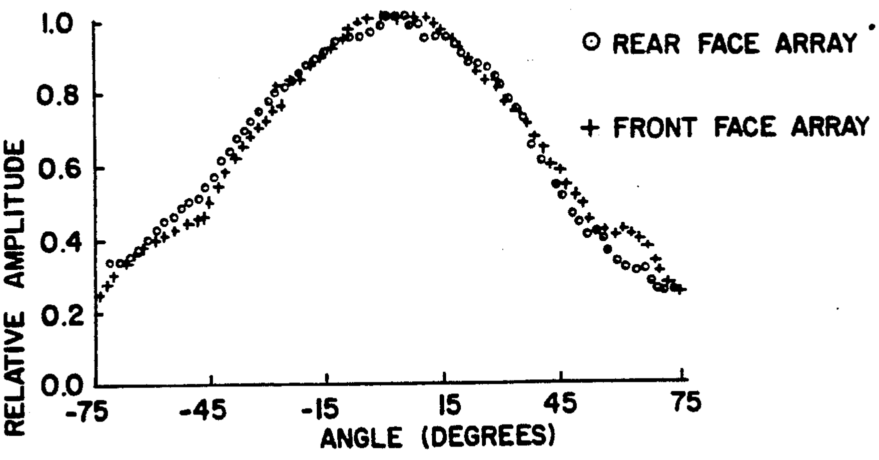

BIPLANE PHASED ARRAY FOR ULTRASONIC MEDICAL IMAGING

BACKGROUND OF THE INVENTION

I. Field of the Invention

This invention relates to ultrasonic transducers in general and more particularly to a biplane phased array ultrasonic transducer arrangement having effectively two arrays of ultrasonic oscillators and electrode patterns on opposite major faces of a piezoelectric material, each array consisting of several acoustically separated transducer elements which are electrically controlled to operate independently. The biplane phased array permits the real time imaging of two planar sectors which can be at any relative angle to another.

II. Description of the Prior Art

Modern ultrasound scanners employ phased array transducers to accomplish electronic steering and focussing of the acoustic beam in a planar sector. These arrays are commonly fabricated from a plate of piezoelectric ceramic by cutting the plate into narrow plank shaped elements. In order to obtain a wide angular response free of grating lobes, the center-to-center element spacing is approximately a half wavelength of sound in tissue at the center frequency.

A novel device combining two orthogonal phased arrays for real time imaging of two orthogonal sectors is disclosed in U.S. patent application Ser. No. 749,613, filed June 27, 1985 entitled "A Biplane Phased Array for Ultrasonic Medical Imaging", Pieter 't Hoen inventor, and assigned to the assignee of the present application, which application is incorporated herein by reference. This application discloses a biplane phased array fabricated by putting an electrode surface on each major surface of a slice of a composite piezoelectric material and scoring the electrode surfaces such that the scoring on one side is at an angle with the scoring on the other side and the scoring does not penetrate the composite material. Appropriate electrical connections are made such that all electrode elements on one electrode surface are grounded and the phasing is performed with remaining free electrodes to image, according to the phased array principle in one direction, and alternately all the electrode elements on the other electrode surface are grounded so that the phasing is performed with the free electrodes on the first side to image in a second direction. The array of transducers is capped on one side by a mechanical lens.

Such a biplane phased array is especially useful in cardiac scanning. Simultaneous horizontal and vertical cross sections of the heart will allow the physician to evaluate more effectively the functioning of the heart. The demonstration of low cross talk in composite piezoelectric arrays suggested the application of composite materials to the design of a biplane phased array.

SUMMARY OF THE INVENTION

This invention proposes a transducer arrangement to extend the phased array principle to the imaging of two orthogonal planes in real time. To achieve this purpose, the present invention uses a composite piezoelectric material which makes possible a crossbar electrode system. A material with negligible cross coupling must be used in the fabrication to make the crossbar electrode pattern feasible. The material is classified as a composite material because it is a laminated structure in which a plurality of relatively small parallel rods of a piezoelectric ceramic material are aligned with the acoustic axis of the transducer, perpendicular to the major surfaces of the plate, and are completely surrounded by an electrically insulating and acoustically damping material. An electrode material is secured to each of the major surfaces of a slice of the composite material. The forming of phased arrays of transducer elements on both of the opposed major faces of the same piece of electric plate requires a new method of defining the transducer array elements, because a complete cutting of the elements as was done in the prior art of conventional phased arrays is not feasible. In the cross referenced application, the array elements were formed by scoring the electrode surfaces only and not the piezoelectric plate, such that the scoring on one side is at an angle with the scoring on the other side.

In the present invention, the transducer array elements are defined by a partial cross dicing technique. The partial cuts on one face of the composite piezoelectric plate define the transducer array elements, while partial cuts on the other face in a different direction, divide each array element into many small subelements with lateral dimensions much smaller than the wavelength. For the preferred embodiment of a biplane phased array as disclosed herewith, the two sets of cuts (or partial dicing) are identical and are rotated by 90°, that is the set of cuts on one major surface is orthogonal to the set of cuts on the second major surface.

While a composite piezoelectric material is utilized in the preferred embodiment, the invention is not limited to such a material.

BRIEF DESCRIPTION OF THE DRAWINGS

FIG. 1*a* is an exaggerated perspective view of a transducer element used in a conventional phased array.

FIG. 1*b* is an exaggerated perspective view of a transducer element in the phased array of the present invention.

FIG. 2 is a partially cut away perspective view of a biplane phased array transducer formed by cross dicing of a piezoelectric plate.

FIG. 4 is a graph showing measured radiation patterns from a single element in a composite phased array defined by an electrode pattern alone.

FIG. 6 is a graph showing a measured radiation pattern from individual elements in a biplane phased array formed by cross dicing the composite plate to 60% of its thickness.

DESCRIPTION OF THE PREFERRED EMDODIMENT

FIG. 1*a* is a side perspective view of a single transducer element of a conventional phased array. Phased array transducers have been traditionally employed to accomplish the electronic steering and focussing of an acoustic beam in a planar sector. Phased arrays are commonly fabricated from a plate of the piezoelectric ceramic by cutting it into narrow plank-shaped elements. In order to obtain a wide angular response free of grating lobes, the center to center element spacing is approximately a half wavelength of sound in tissue at the center frequency.

A novel device combining two orthogonal phased arrays, for the real time imaging of two orthogonal sectors is disclosed in U.S. Pat. application Ser. No. 749,613, filed June 27, 1985, entitled "A Biplane Phased Array for Ultrasound Medical Imaging", Pieter 't Hoen, inventor, and assigned to the assignee of the present application, which application is incorporated herein by reference. The biplane phased array of that application disclosed the use of a composite piezoelectric material having conductive electrode surfaces on both sides. In that application the electrode surfaces are scored to define the individual transducer array elements.

Figure 3:
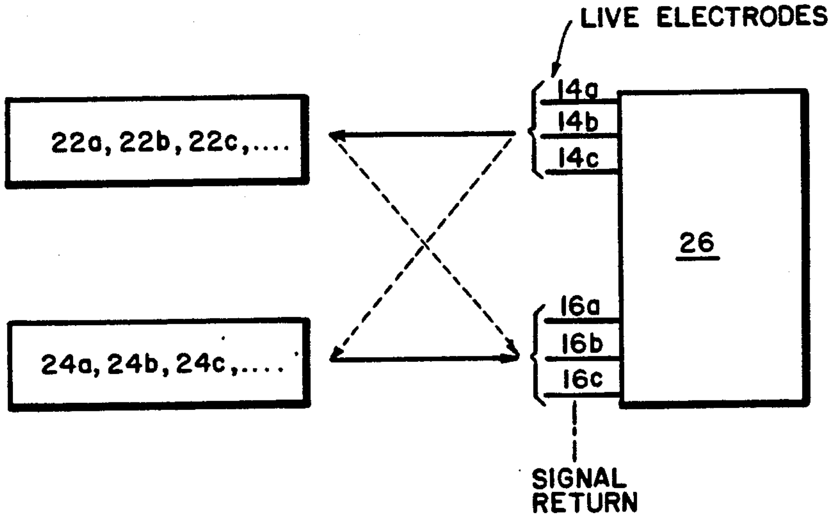
FIG. 3 is a functional diagram of the basic electronic configuration for use with the present invention.

FIGS. 1*b*, 2 and 3 disclose the structure of the improved composite biplane phased array of the present invention. Referring first to FIG. 2, the composite biplane phased array of the present invention consists of a plate 10 of a composite piezoelectric material 12 having two conductive electrodes 14, 16 one of such electrodes being deposited on each of the opposed major surfaces of the plate 10. The composite piezoelectric material is made from a matrix of parallel rods of a piezoelectric ceramic material distributed in an electrically inert binding material such that each of said rods is completely surrounded by the insulating and damping material, the rods extending from one major surface of the plate 10 to the other major surface perpendicular to the major surfaces. Examples of the materials of this type are disclosed in U.S. Pat. Nos. 4,514,247 issued Apr. 30, 1985 and 4,518,889 issued May 21, 1985, both of which are assigned to the assignee of the present application. Such a material is also illustrated and described in the 1984 IEEE ULTRASONIC SYMPOSIUM PROCEEDINGS, published Dec. 19, 1984. The lateral spatial periodicity of the composite piezoelectric structure are smaller than all the relevant acoustic wavelengths. Hence, the composite behaves as a homogeneous piezoelectric with improved effective material parameters as discussed in the article cited above. For purposes of discussion electrode surface 14 will be designated the front face, while the other electrode surface 16 will be designated the back face. When used in an ultrasonic transducer for medical imaging, the front face 14 is the face which is placed towards the body of the patient.

FIG. 2 is a side perspective view of the biplane phased array transducer having a plate of composite piezoelectric ceramic material 12, a front electrode surface 14 and a back electrode surface 16. In the illustration of FIGS. 2 and 3, the biplane phased array transducer is formed by a partial cross dicing of the composite piezoelectric plate 10. Channels 18 are cut in one direction on the front through the front face electrode 14 and partially into the composite piezoelectric material 12 but not completely through the plate. Channels 20 are cut through electrode surface 16 and partially into but not through the composite piezoelectric material 12 at an angle to channels 18. The front electrode transducer elements 22*a*, 22*b*, 22*c*, . . . are obtained by this partial dicing through both the conductive electrode surface and partially through the composite piezoelectric material. Back transducer elements 24*a*, 24*b*, 24*c*, . . . are formed by this partial dicing through the back face electrode 16 and partially through the piezoelectric material 12. Thus, for this biplane phased array, the transducer elements are formed by the partial cross dicing of the composite piezoelectric material, in contrast to the prior art technique of dicing completely through the piezoelectric material and into a backing material used in the construction of conventional phased arrays. While the angle of cross dicing shown in the figures is 90°, other angles may be utilized. In particular, for beam steering in a single plane the second set of cuts can be made at varying angles.

FIG. 3 is a diagrammatic representation of the basic configuration for the electronics required for a biplane phased array. In this figure the reference 26 designates the pulse generator responsible for exciting the transducer elements while the reference numeral 28 represents the ground connection discussed hereinafter. In a biplane phased array according to the present invention, the front face elements 22*a*, 22*b*, 22*c*, . . . and the back face elements 24*a*, 24*b*, 24*c*, . . . are alternately connected to the live electrodes 14, 16 for the signal and the signal return paths. The electronic circuits for phased arrays are known in the art and are not discussed herein because they are not part of and essential to the invention. The phased array circuits are designated generally by the block 26 and they provide the means to pulse alternately all transducer elements on one electrode surface, while grounding the electrodes on the other electrode surface, to effect a sector scan in two planes. In operation, either the front face electrodes or the back face electrodes are grounded and the phasing is performed with the remaining free electrodes. This requires reversing the roles of the electrode sets 14 and 16. Thus an image in one direction is followed quickly by an image in a second direction, producing a dynamic image of a bodily function. Such circuits are well known in the art and are not discussed further herein. For n electrodes on each major surface, a total of 2n electrodes, and two n electrical connections are required to operate the biplane phased array of this invention. The biplane phased array, using both major surfaces of a composite piezoelectric plate, thus permits the near real time imaging of two sector planes. In a usual application, a spherical or at least convex mechanical lens secures focussing in a direction other than that of the transducer arrays. The mechanical lens may be a relatively standard lens which is made from a material from a rather low propagation velocity. The acoustic impedance should not be very different from the skin acoustical impedance to suppress reverberation.

Several trial arrays of the present invention have been tested, having a structure substantially as disclosed in FIGS. 2 and 3, namely having orthogonal arrays on opposite faces of a composite piezoelectric plate such that the radiation profiles from single elements of each array are adequately broad. The results of the tests summarized below indicate that the purpose of the invention is achieved with the elements formed by partially dicing the opposite faces of the composite plate in orthogonal directions.

Experimental Results

This section presents the results of directivity measurements performed on several trial arrays. The interpretation of these results will be discussed separately in the next section.

The trial devices were made from plates of rod composites (resonance frequency 3.5 MHz) in which a Stycast epoxy holds together rods of PZT ceramic (Honeywell #278) oriented perpendicular to the plate face. The PZT rods had a lateral size in the range 54–65 micron with 60 micron spacing between the rods. Array elements (length 12–18 mm) were formed by scribing the electrode or dicing the epoxy between the rods so that each element included two rows of PZT rods. Directivity measurements were performed in a water tank in transmission and reception models using a single resonant pulse excitation.

Undiced Arrays

The first undiced composite array (3.3 MHz, pitch 0.23 mm) was provided with an undiced matching layer of Mylar and air cell backing (FIG. 1). Electrical measurements of cross talk, using a single cycle sinewave excitation, yielded low cross coupling indexes of −26.5, −26, −29.7, and −32 dB for the four nearest neighbors, respectively. However, directivity measurements for a single element in the array (FIG. 1*b*) revealed dips near 36 degrees and peaks near 48 degrees in contrast to the expectation from the diffraction theory for such a narrow radiator.

To investigate the origin of these phenomena a similar array was fabricated without a matching layer and without a backing layer. Directivity measurements for a single element in this array revealed similar patterns with even larger dips and peaks near 38 degrees and 48 degrees, respectively, as shown in FIG. 4. This result indicates that the anomalies in the directivity pattern are associated with the composite material itself.

Further experiments with undiced array elements were performed using a different composite material made with a softer epoxy (Spurr epoxy). A 2 MHz array (pitch 0.45 mm) was formed by scribing the electrode on one face of a Spurr/PZT composite disk. Directivity measurements for a single element in this array shows a broader pattern without side lobes. However, the measured angular beam width is still much smaller than that expected for an isolated element of the same dimensions.

Diced Arrays

Using the Stycast/PZT composites we tried to broaden the radiation pattern by partially dicing the array elements. The first experiment was conducted with a 1.2 MHz composite plate. An array with a pitch of 0.65 mm was formed by dicing the elements to 30% of the plate thickness. The radiation pattern obtained from a single element in this array was the same as the one obtained from an undiced element. However, further experiments showed that a significantly broader beam pattern is obtained when an additional set of orthogonal cuts are made on the other face of the composite plate (FIG. 2). These cross dicing experiments were performed with 3.2 MHz composite plates. Two orthogonal arrays with a pitch of 0.25 mm were formed by dicing the two faces of a composite plate to 30% of its thickness. A 12 micron Kapton foil served as a face plate to keep water from contacting the elements. The radiation profile from a single element (FIG. 5) shows a beam width of 70 degrees at −6 dB which is 50% larger than that obtained with a undiced element.

Further improvement was obtained by cross dicing the elements to 60% of the plate thickness. Detailed directivity measurements were performed with elements belonging to the orthogonal arrays on opposite faces of the composite plate. While exciting an element in the front array (facing the water) all the electrodes on the rear face were connected to the ground. In a similar way, all the electrodes on the front face were grounded while exciting an element in the rear array. The circles and crosses in FIG. 6 show the radiation patterns obtained from a single element in the front array and the rear array, respectively. Both array elements show a broad radiation pattern with an angular width of 96 degrees at −6 dB. This is close to the theoretical beam width of about 100 degrees expected for an isolated element is a soft baffle. A dicing depth of 25–95% of the piezoelectric plate is possible.

Discussion of Experimental Results

Undiced Arrays

The experimental results clearly indicate that the anomalies in the radiation pattern from an undiced phased array element are associated with the acoustic properties of the composite material itself. The combination of ceramic rods and epoxy in a composite structure creates a highly anisotropic material with relatively low acoustic velocities. However, in our present Stycast/PZT composites the acoustic velocities are high as compared to the speed of sound in water. This velocity mismatch creates refraction effects at the composite - water boundary which limit the angular width of the transmitted beam.

Diced Arrays

The partial cross dicing of elements on opposite faces of the composite plate defines two orthogonal arrays with electrical elements divided into many mechanical sub-elements whose lateral dimensions are much smaller than a wavelength (FIG. 1*b*). These small sub-elements radiate and receive acoustic energy at a wide angle because their lateral dimensions are insufficient for the wave phenomena of refraction to occur.

The cross dicing also prevents narrowing of the beam due to cross talk between elements. The cross cuts confine the acoustic path between elements to a set of very narrow strips that act a waveguides. The small transverse dimensions of these waveguides significantly limit the number of propagating modes which they can support.

As a result of the cross dicing the sensitivity of each array is increased because the vibration mode of each array elements is changed from that of a width extensional mode (or "beam mode") of a plank to that of a length extensional mode of a set of bars. In the Stycast/PZT composites we found that the coupling factor of an array element is increased from 0.59 to 0.65 after 60% dicing in orthogonal directions.

CONCLUSION

Feasibility of a biplane phased array is indicated by the broad single-element directivity measured on a 3 MHz array formed by partially dicing the elements on opposite face of a composite plate in orthogonal directions.

The narrow radiation profile of phased array elements define on composites by electrode patterning alone was shown to be due to the high acoustic velocities in the present composite material.

The advantages of this structure of a composite biplane phased array are as follows:

1. Sensitivity: As a result of the cross dicing, the vibration mode of each array element is changed from that of a width extensional mode (or "beam mode") of a plank to that of a length extensional mode of a set of bars. The electromechanical coupling factor $k_{33}$ associated with the latter is larger that that $k'_{33}$ associated with the former. For example in PZT-5, $k_{33}=0.705$ while $k'_{33}=0.66$.

2. Angular response: The cross cuts confine the acoustic path between elements to a set of very narrow strips that act as waveguides. The small transverse dimensions of these waveguides significantly limit the number of propagating modes which they can support The cross dicing also reduces narrowing of the angular response caused by refraction effects. The small sub-elements formed by the cross dicing can radiate and receive acoustic energy at a wide angle because their lateral dimensions are insufficient for the wave phenomena of refraction to occur.

3. Rigidity: The structure obtained by a partial cross dicing is rigid and need not be supported by a backing layer. The elimination of a backing layer improves the sensitivity and reduces cross coupling.
4. Versatility: The partial cross dicing technique can be applied to the fabrication on conventional phased arrays, bi-plane phased arrays, and two dimensional arrays.

Figure 5:
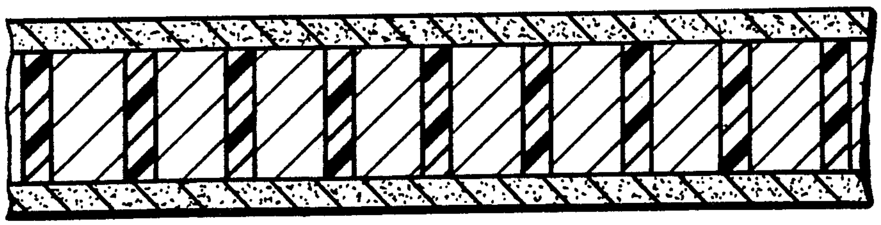
FIG. 5 is a graph showing the measured radiation from a single element in a phased array formed by cross dicing the composite plate to 30% of its thickness.

The cross dicing technique was tested experimentally using a composite piezoelectric material. Phased arrays (3 MHz, half-wavelength pitch) with elements defined by an electrode pattern alone showed anomalies in the directivity pattern for a single element as shown in FIG. 4. Cross dicing of the array elements to 30% of the thickness of the composite plate yielded improved results as shown in FIG. 5. Cross dicing to a depth of 60% yielded the result shown in FIG. 6. This result agrees with the theoretical expectation for the directivity of an isolated element in a soft baffle.

I claim:

1. An array transducer for ultrasonic medical imaging comprising:

a plate of a piezoelectric material having plural major surfaces;

a conductive electrode material laminated on each of the major surfaces of said plate, forming electrode surfaces thereon;

each major surface of said piezoelectric plate being diced through its electrode surface and partially through the piezoelectric material to provide a matrix of acoustically separated transducer elements, the partial dicing of one of said major surfaces being at an angle to the partial dicing of the second of said major surfaces;

means to connect alternately all electrode elements on one major transducer surface with phased array electronics while grounding the electrode elements of the other major transducer surface to effect a sector scan alternately in each of said two planes, such that in image in one direction is followed immediately by an image in a second direction, thus producing a dynamic image of a bodily function.

2. The array transducer of claim 1, wherein said piezoelectric material is a composite material having elements of a piezoelectric ceramic material imbedded therein, each of said elements extending from one major surface of said plate to the other major surface of said plate perpendicularly to said major surfaces, each of said elements being completely surrounded by an electrically insulating and damping material.

3. A array ultrasonic transducer comprising:

a plate of a composite piezoelectric ceramic material having two major surfaces, each major surface being diced partially through the said composite piezoelectric ceramic material;

a plurality of adjacent electrode elements formed by said partial dicing exposed on each of said two major surfaces, those electrode elements on a first surface being at an angle to those electrode elements on the second surface, the portion of said plate underlying each of said electrode elements defining a separate transducer element;

electrical circuit means connecting lines to each of said electrode elements such that when the electrode elements on one of said major surfaces are active, the lines to the electrode elements on the other major surface are grounded;

means to connect alternately all electrode elements on one electrode surface with phased array electronics while grounding the electrode elements on the other major electrode surface to effect alternately a sector scan in each of the two planes, such that an image in one direction is followed immediately by an image in a second direction, thus producing a nearly dynamic image of a bodily function.

4. The array transducer of claim 1, 2 or 3 wherein the dicing of said major surfaces penetrates 30% of the depth of said piezoelectric plate.

5. The array transducer of claim 1, 2 or 3 wherein the dicing of said major surfaces penetrates the piezoelectric plate to 60% of the depth of said piezoelectric plate.

6. The array transducer of claim 1, 2 or 3 wherein the dicing of each of said major surfaces penetrates from 25–95% of the depth of said piezoelectric plate.

* * * * *